(12) United States Patent
Hickey et al.

(10) Patent No.: US 9,034,617 B2
(45) Date of Patent: May 19, 2015

(54) PROCESSES FOR THE ANAEROBIC BIOCONVERISON OF SYNGAS TO OXYGENATED ORGANIC COMPOUND WITH IN SITU PROTECTION FROM HYDROGEN CYANIDE

(71) Applicant: COSKATA, INC., Warrenville, IL (US)

(72) Inventors: Robert Hickey, Okemos, MI (US); Jianxin Du, Naperville, IL (US); Andrew Reeves, Chicago, IL (US); Richard E. Tobey, St. Charles, IL (US)

(73) Assignee: Coskata, Inc., Warrenville, IL (US)

( * ) Notice: Subject to any disclaimer, the term of this patent is extended or adjusted under 35 U.S.C. 154(b) by 0 days.

(21) Appl. No.: 13/828,542

(22) Filed: Mar. 14, 2013

(65) Prior Publication Data
US 2014/0273125 A1 Sep. 18, 2014

(51) Int. Cl.
*C12P 7/16* (2006.01)
*C12P 7/06* (2006.01)
*C12P 7/04* (2006.01)

(52) U.S. Cl.
CPC ... *C12P 7/16* (2013.01); *C12P 7/04* (2013.01); *C12P 7/06* (2013.01)

(58) Field of Classification Search
CPC ............... C12P 7/16; C12P 7/06; C12P 7/04
USPC .......................................... 435/160, 161, 157
See application file for complete search history.

(56) References Cited

U.S. PATENT DOCUMENTS

| | | | |
|---|---|---|---|
| 4,162,970 A * | 7/1979 | Zlokarnik ..................... 210/620 |
| 5,705,072 A | 1/1998 | Haase | |
| 5,976,868 A | 11/1999 | Buisman | |
| 7,655,205 B2 | 2/2010 | Van Grinsven et al. | |
| 8,128,898 B2 * | 3/2012 | Van Dyk et al. ............. 423/236 |
| 8,211,679 B2 | 7/2012 | Datta et al. | |
| 2009/0134008 A1 | 5/2009 | White et al. | |

OTHER PUBLICATIONS

Xu et al., The effects of syngas impurities on syngas fermentation to liquid fuels. Biomass and Bioenergy, vol. 35 (2011) pp. 2690-2696.*
Bredwell et al., Reactor design issues for synthesis-gas fermentations. Biotechnology Progress, vol. 15 (1999) pp. 834-844.*
Banfalvi, Gaspar, "Removing Cyanide From Waterways", Chemical Innovation, Oct. 2000, vol. 30, No. 10, 53-54.

* cited by examiner

*Primary Examiner* — Jon P Weber
*Assistant Examiner* — Kara Johnson

(57) ABSTRACT

Processes are disclosed for the anaerobic bioconversion of syngas to oxygenated organic compound that use an in situ method for protecting the microorganisms from hydrogen cyanide contained in the syngas that passes to the fermentation broth. The fermentation broth is maintained at a pH of between about 4 and 6, and dissolved metal cation of one or more of iron, cobalt, nickel and zinc is provided to the fermentation broth in an amount sufficient to form, under the conditions of the fermentation broth, a substantially insoluble metal complex with the metal cation and cyanide anion. The rate of formation of the insoluble complex is sufficiently high that that the amount of cyanide that is taken up by microorganisms does not result in an undue adverse effect on the population of microorganisms.

19 Claims, 1 Drawing Sheet

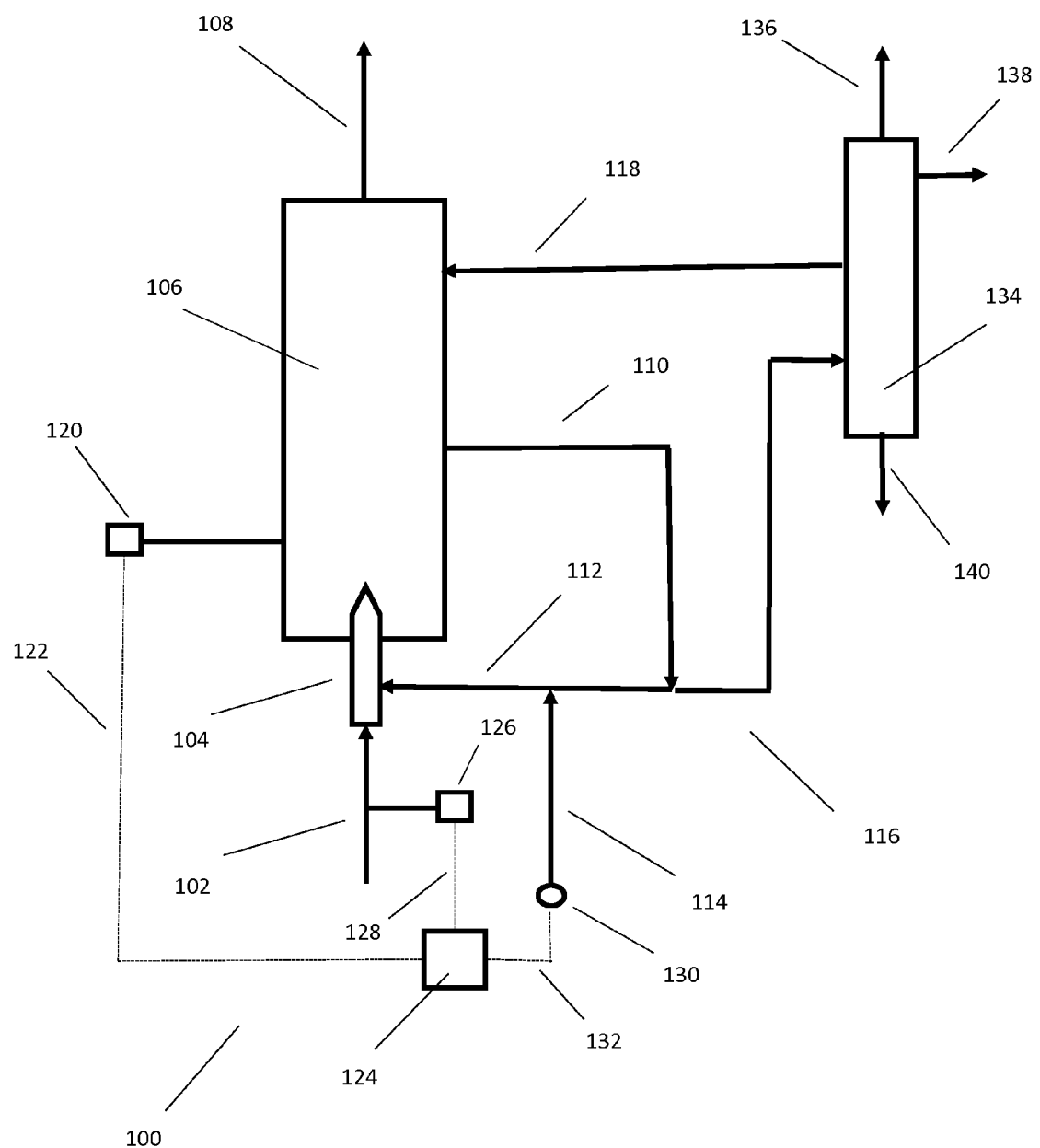

US 9,034,617 B2

PROCESSES FOR THE ANAEROBIC BIOCONVERISON OF SYNGAS TO OXYGENATED ORGANIC COMPOUND WITH IN SITU PROTECTION FROM HYDROGEN CYANIDE

FIELD OF THE INVENTION

This invention relates to processes for anaerobically bioconverting syngas to an oxygenated organic compound in a fermentation broth containing microorganisms, and particularly to such processes which provide an in situ protection of the microorganisms from any hydrogen cyanide contained in the syngas.

BACKGROUND

Biofuels production for use as liquid motor fuels or for blending with conventional gasoline or diesel motor fuels is increasing worldwide. Such biofuels include, for example, ethanol, propanol, i-butanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bio-ethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion.

One available technology path to convert lignocellulosic biomass to ethanol is to convert lignocellulosic biomass to syngas (also known as synthesis gas) in a gasifier and then ferment this gas with anaerobic microorganisms to produce biofuels such as ethanol, propanol, i-butanol and n-butanol or chemicals such as acetic acid, butyric acid and the like. This technology path can convert all of the components to syngas with good efficiency (e.g., greater than 75% of the energy content is recovered as carbon monoxide and hydrogen), and some strains of anaerobic microorganisms can convert syngas to ethanol, propanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste, land fill gas and biogas, and be obtained as an off gas from other industrial processes, making this a more universal technology path.

However, production of syngas from carbonaceous feedstocks can result in the generation of hydrogen cyanide as a contaminant that is detrimental to the biological conversion of the syngas to oxygenated organic compound. Hydrogen cyanide must be removed from syngas and then managed or destroyed in an environmentally acceptable manner, generally at significant expense.

Since the syngas may contain undesired contaminants in addition to hydrogen cyanide, methods for treating the syngas to remove hydrogen cyanide must also take into account other components of the syngas, some of which may be beneficial or substantially inert in the fermentation process and some of which may be detrimental to the microorganisms.

Numerous processes are known for removing hydrogen cyanide from gases. Conventional methods for removal of hydrogen cyanide from syngas prior to its use generally involves scrubbing with aqueous solutions to remove these compounds from the syngas with subsequent discharge of the scrubbing solutions to wastewater treatment or via alternate disposal methods. Other methods include catalytic sorption, adsorption, condensation with aldehydes, and reaction with metal cations such as iron, cobalt, nickel, copper and the like. See, for instance, United States Published Patent Application No. 20110097701 A1, and U.S. patent application Ser. No. 13/304,902, filed on Nov. 28, 2011, disclosing the use of peroxygenated reactants, both hereby incorporated by reference in their entirety. Van Dyk, et al., in U.S. Pat. No. 8,128, 898 B2, disclose processes for the removal of hydrogen cyanide from synthesis gas using a scrubbing solution containing at least one dissolved metal salt. The metal cations are capable of forming metal cyanide complexes or precipitates and include one or more of iron, copper, cobalt, silver, gold or other transition metal cations. A buffer is used to maintain the scrubbing solution in a pH range of between 6 and 10. The salts are preferably present in a concentration in the scrubbing solution at about 1 to 20 mass percent. Haese in U.S. Pat. No. 3,950,492, discloses processes for removing hydrogen sulfide and hydrogen cyanide from gases using an aqueous iron salt washing solution formed from at least one acid selected from the group consisting of sulfuric acid and sulfurous acid.

Banfalvi in "Removing cyanide from waterways", Chemscripts, October 2000, Vol. 30, No 10, 53-55, reviews several methods for removal of cyanide, e.g., from mining extraction operations, from rivers. Conversion of cyanide to thiocyanide was dismissed by the author since the conversion requires energy. The use of iron salts was found to be problematic as ferricyanide complexes can be toxic to some aquatic life, and the use of chlorine to generate oxygen for converting hydrogen cyanide to cyanic acid is unacceptable due to the toxicity of chlorine. The author proposes the use of carbon dioxide to generate carbonic acid and release hydrogen cyanide from cyanide salts which can evaporate or be oxidized to cyanic acid.

For an oxygenated organic compound fermentation process to be commercially viable, capital and operating costs must be sufficiently low that it is at least competitive with alternative biomass to oxygenated organic compound processes. For instance, ethanol is currently commercially produced from corn and cane sugar in facilities having name plate capacities of over 100 million gallons per year at sufficiently low costs to be competitive with fossil fuels. Commercial-scale bioreactors thus often have capacities of greater than 1 million, and more frequently greater than about 5 or 10 million, liters in order to capture economies of scale.

Although methods are well known for removing hydrogen cyanide from gases, the operation of commercial-scale fermentation facilities to convert the syngas to an oxygenated organic compound cannot tolerate a failure of the hydrogen cyanide removal unit operation due to the adverse impact of the failure on the population of microorganisms in the fermentation broth. In general, microorganisms used for the anaerobic bioconversion of syngas to oxygenated organic compound are sensitive to the presence of hydrogen cyanide and often hydrogen cyanide concentrations in the fermentation broth must be maintained below about 100, and sometimes less than 10, parts per billion mass per volume. The economic cost of a failure of the hydrogen cyanide removal unit operations on such a commercial process can readily be appreciated when it is realized that repopulating a bioreactor with microorganisms to achieve steady-state operation may take 5 to 10 days. Moreover, if the fermentation broth has to be discarded due to the presence of hydrogen cyanide, losses of nutrients and other adjuvants would be incurred.

The use of redundant hydrogen cyanide removal unit operations to avoid a break through or address a failure of the hydrogen cyanide removal unit operation adds to the capital and operating expense of facility. Accordingly, processes are sought to protect the population of microorganisms in an anaerobic bioreactor used to convert syngas to oxygenated organic compound in the event of a hydrogen cyanide break through or failure of the hydrogen cyanide removal unit operation, which processes are not only effective but also do not require undue capital and operating expense to implement. Most desirably such processes would be in situ processes in the fermentation broth to avoid an additional unit operation dedicated solely to hydrogen cyanide removal. However, such processes must be effective without adversely affecting the microorganisms or the bioconversion of syngas to oxygenated organic product.

SUMMARY OF THE INVENTION

In accordance with this invention it has been found that the population of microorganisms for the anaerobic bioconversion of syngas to an oxygenated organic compound can be protected from hydrogen cyanide, whether by breakthrough or failure of an upstream hydrogen cyanide removal unit operation or from untreated syngas having a very small concentration of hydrogen cyanide, by an in situ method involving the use of the fermentation broth itself. By this invention it has been surprisingly found that making the hydrogen cyanide inert can occur sufficiently rapidly in an in situ process such that the population of microorganisms in the fermentation broth is not unduly adversely affected by such hydrogen cyanide. Moreover, the in situ method of this invention does not adversely affect the microorganisms or the bioconversion rate of syngas to the oxygenated organic compound.

The processes of this invention pertain to the use of an situ method for protecting the population of microorganisms from hydrogen cyanide wherein the fermentation broth is maintained at a certain, lower pH conditions and involve employing certain dissolved metal cations in the fermentation broth. It is surprising that at these lower pH conditions, the metal cations quickly form stable, insoluble complexes with cyanide anion. Since the rate at which these insoluble complexes are formed is relatively high as compared to the rate of uptake of cyanide by the microorganisms, adequate protection of the population of microorganisms can occur even though cyanide is introduced into the fermentation broth. Moreover, even a relatively low concentration of these metal cations in the fermentation broth can avoid undue damage to the population of microorganisms in the fermentation broth.

In its broad aspects, the processes of this invention pertain to the anaerobic bioconversion of gas substrate comprising carbon monoxide, hydrogen and carbon dioxide to an oxygenated organic compound in a fermentation broth wherein said gas substrate may contain from time to time hydrogen cyanide comprising:

a. continuously introducing said gas substrate into a fermentation broth containing microorganisms suitable for bioconverting said substrate to oxygenated organic compound, said fermentation broth being maintained under anaerobic fermentation conditions, and the gas substrate having sufficient contact with the fermentation broth to provide an oxygenated organic compound-containing fermentation broth and a substrate-depleted gas phase;

b. maintaining the pH of the fermentation broth between about 4 and 6, preferably between about 4.3 and 5.5, say between about 4.5 and 5;

c. continuously or intermittently supplying to said fermentation broth a metal cation of one or more of iron, cobalt, nickel and zinc, preferably iron and cobalt, and especially ferrous cation, capable of forming a substantially water insoluble complex with a cyanide anion, to provide said metal cation dissolved in said fermentation broth in an amount at least stoichiometrically sufficient to form, under said anaerobic fermentation conditions and pH, said water insoluble complex with the cyanide anion if introduced with said gas substrate into said fermentation broth;

d. continuously withdrawing the substrate-depleted gas phase from the fermentation broth having a substantial absence of the hydrogen cyanide; and e. continuously or intermittently withdrawing a portion of the fermentation broth for recovery of said oxygenated organic compound, said withdrawal being sufficient to maintain the oxygenated organic compound in said fermentation broth below a concentration that unduly adversely affects the microorganisms.

The preferred concentration of the metal cation in the fermentation broth will in part be determined by the anticipated rate of hydrogen cyanide passing to the fermentation broth in the event of a breakthrough or normally in the gas substrate where the in situ process serves as a unit operation for the removal of hydrogen cyanide. The potential concentration of hydrogen cyanide in the gas substrate will depend upon the source of the gas substrate. In general, the processes of this invention can address gas substrates containing 30 or more parts per million by volume hydrogen cyanide. The processes are particularly attractive with gas substrates that can contain up to about 20 or 25, preferably up to about 10, parts per million by volume hydrogen cyanide. The flow rate of gas substrate per unit volume of the fermentation broth can also vary over a wide range and will depend upon the bioconversion rate per unit volume of the fermentation broth; the composition of the gas substrate, particularly the concentration of hydrogen, carbon monoxide and carbon dioxide; and operator flow rate selection. Frequently the concentration of dissolved metal cation in the fermentation broth is at least about 0.01, say, between about 0.25 and 0.5, preferably between 0.05 and 0.2, milligram atoms per liter.

In the processes of this invention, at least a portion, and preferably at least about 90, most preferably at least about 99, percent of the hydrogen cyanide introduced into the fermentation broth is reacted with the metal cation to form a substantially insoluble complex or reaction product of the metal and the cyanide (herein referred to as "water insoluble complex"). The water insoluble complex can be removed from the fermentation broth in any suitable manner, e.g., by withdrawing a portion of the fermentation broth containing suspended cyanide-containing solids. Generally these solids are removed in step (e) and separated with a solids-containing fraction generated during the processing to recover oxygenated organic compound from the fermentation broth.

In one aspect of the invention, the rate of introduction of the at least one metal cation is sufficient to maintain a substantially constant concentration of metal cation in the fermentation broth. In another aspect of the invention, the concentration of hydrogen cyanide in the gas substrate and/or the rate of gas substrate being passed to the fermentation broth is determined (net hydrogen cyanide flow rate) and the rate of addition of the metal cation is adjusted in response the determined concentration of hydrogen cyanide and/or the determined flow rate of the gas substrate to provide sufficient metal cation to complex or react with the cyanide. Typically, in this other aspect of the invention, at least about 0.42, preferably at least about 0.5, and frequently between about 0.5 and 1, gram atoms of metal cation are provided per unit time per mole of hydrogen cyanide contained in the gas substrate introduced per unit time into the fermentation broth. In some instances, the metal cation may be taken up by the microorganisms. This up-take needs to be taken into account when determining the minimum amount of metal cation to be added. Preferably the fermentation broth contains a concentration of dissolved metal cation, and the changes in the rate of addition of the metal cation accommodates changes in hydrogen cyanide being introduced into the fermentation broth.

In preferred embodiments of the processes of this invention, the gas substrate is injected into the fermentation broth using a motive fluid and a metal cation is contained in the motive fluid. Typically at least a portion, and often a major portion, of the motive fluid comprises fermentation broth with the remainder typically being make-up for the fermentation broth. Thus the motive fluid may contain the metal cation for the removal of a cyanide anion. More preferably, any make-up metal cation and any metal cation for increasing the concentration of the metal cation, whether to achieve a steady state concentration in the fermentation broth or to adjust the concentration of metal cation accommodates an increase in the net hydrogen cyanide flow rate. Even though the duration of contact between the gas substrate and the motive fluid may be relatively short, the rate of mass transfer of hydrogen cyanide to the liquid phase and the rate of reaction to form the substantially insoluble solid are typically sufficiently rapid that at least a portion of the hydrogen cyanide is removed from the gas substrate prior to introduction into the fermentation broth.

The processes of this invention may be used continuously during the duration of the fermentation or may be used from time-to-time as needed or as the risk of hydrogen cyanide passing into the fermentation broth increases. For instance, if the source of the syngas is changed with a higher potential concentration of hydrogen cyanide being contained therein, or if the unit operation for removal of hydrogen cyanide is failing or has failed, the processes of this invention may be commenced and then terminated when the risk of hydrogen cyanide breakthrough to the fermentation broth has abated. A particularly valuable application of the processes of this invention is during start-up of a bioreactor where the density of microorganisms is significantly lower than at normal steady-state operation. Due to the low concentration of microorganisms, any hydrogen cyanide breakthrough to the fermentation broth would take a proportionately higher toll on the population of microorganisms, and any reduction in microorganism population would increase the time required to achieve the desired steady-state population. Accordingly, during this period of time, a greater concentration of metal cation may be used in the fermentation broth than is used during steady-state operation, e.g, at least about 10, and sometimes between about 20 and 500, percent greater.

BRIEF DESCRIPTION OF THE DRAWING

FIG. 1 is a schematic depiction of an apparatus suitable for practicing processes in accordance with this invention.

DETAILED DISCUSSION

Definitions

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the fermentation broth.

Fermentation broth means a liquid water phase which may contain dissolved compounds including, but not limited to hydrogen, carbon monoxide, and carbon dioxide.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

Intermittently means from time to time and may be at regular or irregular time intervals.

Deep tank bioreactor is a bioreactor having a depth of at least about 10 meters and can be operated to provide a substantial non-uniform substrate composition over the depth of the fermentation broth contained in the bioreactor. The term bubble column bioreactor as used herein refers to a deep tank bubble column bioreactor unless otherwise explicitly stated. A commercial scale bioreactor has a fermentation broth capacity of at least 1 million, and more preferably at least about 5, say, about 5 to 25 million, liters.

A concentration of oxygenated organic compound below that which unduly adversely affects the rate of growth of the population of microorganisms will depend upon the type of microorganism and the oxygenated organic compound. An unduly adverse effect on the growth rate means that a significant, usually at least a 20 percent, decrease in the growth rate of the microorganisms is observed.

The abbreviation ppm means parts per million. Unless otherwise stated or clear from the context, ppm is on a mole basis (ppm (mole)).

Syngas means a gas containing at least one of hydrogen and carbon monoxide and may, and usually does, contain carbon dioxide.

The use of the terms "a" and "an" is intended to include on or more of the element described.

Overview

The processes of this invention pertain to the anaerobic bioconversion of syngas to oxygenated organic compound using an in situ method to protect the microorganism population from hydrogen cycanide.

Syngas Generation

The source of the syngas is not critical to the broad aspects of this invention. Gasification, partial oxidation, and reforming (autothermal and steam) of biomass or fossil carbonaceous materials can be used. Gasification and partial oxidation processes are disclosed in copending U.S. patent application Ser. No. 13/304,902, filed on Nov. 28, 2011, hereby incorporated by reference in its entirety. Rice, et al, in "Autothermal Reforming of Natural Gas to Synthesis Gas", Reference: KBR Paper #2031, Sandia National Laboratories, April 2007, discuss autothermal reforming and conditions. Steam reforming is a widely practiced commercial unit operation. See Logdberg, et al., "Natural Gas Conversion", Haldor Topsoe publication (undated). Reforming in the presence of carbon dioxide is known as carbon dioxide reforming with the partial pressure of carbon dioxide causing a shift in the product distribution of the reforming. See, for instance, Madsen, et al, "Industrial Aspects of $CO_2$-reforming", Paper No. 28f, presented at the AIChE Spring Meeting, Houston, Tex., March 1997. Reforming is a temperature dependent equilibrium reaction, and thus the addition of hydrogen, carbon monoxide or carbon dioxide will affect the distribution of steam, hydrogen, carbon monoxide and carbon dioxide from the fresh feed although the distribution in the produced syngas will be set by the thermodynamic equilibria.

Where a source of carbon dioxide is available, steam reforming is generally preferred due to the high hydrogen concentration of the produced syngas and the relative absence of contaminants that must be removed to prevent deleterious effects on the microorganisms for the anaerobic bioconversion to alcohol. Additionally, steam reforming, being non-oxidative, provides a syngas that is relatively free of nitrogen which would be present in the syngas produced by a partial oxidation or autothermal reforming process using air or enriched air as the oxygen source. Another advantage of steam reforming is that the depleted gas phase from the bioreactors can be used as a portion of the fuel required for providing the heat for the steam reforming. By using the depleted gas phase to provide heat, and offset of fresh carbonaceous feed occurs and thereby enhances the net conversion of fresh carbonaceous feed to alcohol. The portion of the carbonaceous feed that can be offset will depend upon the volume and heating value of the depleted gas phase.

Since the unit operations to make the syngas can vary widely, it is understood that the compositions of the syngas may similarly vary widely including the presence of components other than hydrogen, carbon monoxide and carbon dioxide, which components may be inert such as nitrogen and methane or components that may have to be removed due to potential adverse effects on the microorganisms such as hydrogen cyanide. Processes for removing adverse components include those disclosed in U.S. patent application Ser. No. 13/304,902, filed on Nov. 28, 2011; Ser. No. 13/440,953, filed on Apr. 5, 2012; and Ser. No. 13/525,079, filed on Jun. 15, 2012; and U.S. Pat. No. 7,927,513 filed on Oct. 27, 2009 and U.S. Pat. No. 8,303,849, filed on Nov. 9, 2010, all hereby incorporated by reference in their entireties. Also, the relative ratios among hydrogen, carbon monoxide and carbon dioxide may vary widely. An advantage of the control system of the processes of this invention is that such variations in the relative ratios can be accommodated to provide a substrate gas to the bioreactor assembly that enables achieving a high conversion of hydrogen and carbon monoxide to alcohol. In some instances, more than one source of syngas may be used.

As stated above, the concentration of hydrogen cyanide in the gas substrate introduced into the fermentation broth can vary depending upon source of the syngas and upon the unit operations and their efficacies for removal of hydrogen cyanide prior to the introduction of the gas substrate into the fermentation broth. Thus, the gas substrate may contain virtually no hydrogen cyanide, e.g., less than about 1 parts per billion by volume and the processes are used to prevent a loss of microorganisms in the unplanned event of a hydrogen cyanide excursion, or the gas substrate may contain upwards of 30 or more parts per million by volume.

Oxygenated Organic Compound, Microorganisms and Fermentation Conditions

The oxygenated organic compounds produced in the processes of this invention will depend upon the microorganism used for the fermentation and the conditions of the fermentation. One or more microorganisms may be used in the fermentation broth to produce the sought oxygenated organic compound. Bioconversions of CO and $H_2/CO_2$ to acetic acid, propanol, butanol, butyric acid, ethanol and other products are well known. For example, in a recent book concise descriptions of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any suitable microorganisms that have the ability to convert the syngas components, CO, $H_2$, $CO_2$, individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edmond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No. 12/272,320 on Mar. 19, 2010. All of these references are incorporated herein in their entirety.

Suitable microorganisms for bioconversion of syngas to oxygenated organic compounds generally live and grow under anaerobic conditions, meaning that dissolved oxygen is essentially absent from the fermentation liquid also referred to as a broth or aqueous broth. Adjuvants to the aqueous broth may comprise buffering agents, trace metals, vitamins, salts etc. Adjustments in the broth may induce different conditions at different times such as growth and non-growth conditions which will affect the productivity of the microorganisms. U.S. Pat. No. 7,704,723, hereby incorporated by reference in its entirety, discloses the conditions and contents of suitable aqueous broth for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous broth composition, and syngas residence time, are preferably sufficient to achieve the sought conversion efficiency of hydrogen and carbon monoxide and will vary depending upon the design of the fermentation reactor and its operation. The pressure may be subatmospheric, atmospheric or super atmospheric, and is usually in the range of from about 90 to 1000 KPa absolute and in some instances higher pressures may be desirable for biofilm fermentation reactors. As most reactor designs, especially for commercial scale operations, provide for a significant height of aqueous broth for the fermentation, the pressure will vary within the fermentation reactor based upon the static head.

The fermentation conditions are preferably sufficient to effect at least about 40 or 50 percent conversion of the carbon monoxide in gas feed. For commercial operations, the fermentation operation preferably provides a total molar conversion of hydrogen and carbon monoxide in the net gas feed in the range of about 85 to 95 percent. Due to the low solubilities of carbon monoxide and hydrogen in the aqueous phase, achieving these high conversions may require using one or more of multiple fermentation reactors and recycling off gas from a reactor. Typically in the case of multiple fermentation reactors in gas flow series it is only necessary to apply the processes of the invention to the first fermentation reactors.

The rate of supply of the gas feed under steady state conditions to a fermentation reactor is such that the rate of transfer of carbon monoxide and hydrogen to the liquid phase matches the rate at which carbon monoxide and hydrogen are bioconverted. Hence, the dissolved concentration of carbon monoxide and hydrogen in the aqueous phase remains constant, i.e., does not build-up. The rate at which carbon monoxide and hydrogen can be consumed will be affected by the nature of the microorganism, the concentration of the microorganism in the aqueous broth and the fermentation conditions. As the rate of transfer of carbon monoxide and hydrogen to the aqueous broth is a parameter for operation, conditions affecting the rate of transfer, such as interfacial surface area between the gas and liquid phases and driving forces, are important.

Preferably the substrate gas is introduced into the fermentation broth in the form of microbubbles. Often the microbubbles have diameters in the range of 0.01 to 0.5, preferably 0.02 to 0.3 millimeter. Preferably the substrate gas is injected using a motive fluid. Variations in the motive liquid flow rate can be used to modulate the microbubble size and thus modulate the rate of transfer of carbon monoxide and hydrogen to the liquid phase. Moreover, the modulation provides microbubbles that provide a stable gas-in-liquid dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the range of cross-sectional dimensions in the case of jet injectors or as the smaller range of cross-sectional dimensions in the case of slot injectors. The bubble size generated by the injectors will be influenced by, among other factors, the rate of liquid flow through the injector and the ratio of gas phase to liquid phase passing through the injector as well as the characteristics of the aqueous broth itself including, but not limited to, its static liquid depth. See also, U.S. patent application Ser. No. 13/243,062, filed on Sep. 23, 2011. In some instances the microbubbles, which form a less dense gas-liquid dispersion and any motive fluid used to generate the microbubbles, can facilitate liquid mixing in a bioreactor.

Bioreactors

The bioreactors used in this invention may comprise one or more bioreactors which may be, with respect to gas flow, in parallel or in series flow. Each bioreactor may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

Metal Cations and Introduction into the Fermentation Broth

The metal cations used in the processes of this invention are one or more of iron, cobalt, nickel and zinc, preferably iron and cobalt, especially ferrous cation. The metal cations used form complexes that at the pH of the fermentation broth are substantially water insoluble and thus effectively inert the hydrogen cyanide. Also, the metals are relatively non-toxic to the microorganism and, especially iron, are required by the microorganisms for metabolic activity. The rate that the metal cation complexes with the cyanide anion may also be important as describe above. The metal cations used exhibit a strong ability to form the cyanide complexes and thus have desired reaction rates.

The metal cations are typically provided by a water soluble salt which may be organic or inorganic. Due to the low concentrations that are effective in the processes of this invention, the metal compound used may need only be sparingly soluble in the fermention broth. Representative metal compounds include, but are not limited to, metal carboxylates such as metal formate and metal acetate; metal alkoxides, such as metal methoxide, metal ethoxide, and inorganic metal salts, e.g., halides such as metal chlorides; metal nitrates; and the like.

The metal cation may be added to the fermentation broth in any convenient manner. For instance, it may be added as a solid compound and then dissolved in the fermentation broth or, preferably, may be dissolved in a liquid which is then added to the fermentation broth. In the more preferred embodiments of this invention, the metal cation is added either as a solid or preferably dissolved in an aqueous liquid, e.g. to motive fluid mixed with the gas substrate for introduction into the fermentation broth. In this latter case, at least a portion of the hydrogen cyanide may form insoluble metal complexes prior to injection into the fermentation broth.

In the embodiments of this invention where a sought dissolved metal concentration in the fermentation broth is desired, the rate of introduction of metal cation may be controlled based upon an analysis of the fermentation broth. The analysis may be conducted by any suitable technique as is well known in the art. At steady-state conditions, the amount of metal cation added may be based upon the expected loss of metal cation with, e.g., product recovery and up-take by microorganisms, and adjustments made periodically or intermittently based upon analyses. In embodiments of this invention where the amount of metal cation added is based upon a measurement of hydrogen cyanide in the gas substrate being introduced into the fermentation broth, it is preferred that sufficient time exists between the determination of the hydrogen cyanide flow rate and its introduction into the fermentation broth. This allows the flow rate of the metal cation to be adjusted according to an at least partially equilibrated flow rate of metal cation introduction. An advantage of introducing the metal cation into a motive fluid for introducing the gas substrate into the fermentation broth is that the increase in metal cation concentration occurs at the region where the gas substrate having an increased concentration of hydrogen cyanide is first being introduced into the fermentation broth. Hence, additional protection is provided to the population of microorganisms.

Without wishing to be limited to theory, it is believed that an equilibrium exists relating to the reaction of the metal cation with cyanide anion to form a complex anion of the formula $Me(CN)_6^{-x}$ wherein Me is the metal cation and x is the valence of the anion. This anion then is involved in an equilibrium reaction with further metal cation to form a precipitate of the metal cation and the complex anion. The shift of the equilibrium towards the precipitate are primarily influenced by the pH of the fermentation broth and concentration of metal cation in the fermentation broth. Accordingly, the concentration of the metal cation in the fermentation broth is maintained in excess of that required for the stoichiometric reaction to form the complex. Often, the metal cation is present in a concentration at least about 2, and preferably at least about 10, say, between about 10 and 50, times that required for the stoichiometric reaction to form the precipitate.

Product Recovery

The fermentation vessel may have added from time to time or continuously one or more streams of water, nutrients or adjuvants, and microorganisms. A portion of the aqueous broth is withdrawn from time to time or continuously from the bioreactor for product recovery. Usually, the withdrawal is made at a point at the upper portion of the aqueous broth in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679, herein incorporated by reference in its entirety, shows an arrangement for product recovery from a bioreactor that recovers an ethanol product from a bioreactor.

Drawings

A general understanding of the invention and its application may be facilitated by reference to the FIGURES. The FIGURES are not in limitation of the broad aspects of the invention.

FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the production of ethanol. The process is readily adaptable to making other oxygenated organic compounds including, but not limited to, alcohols such as i-butanol, n-butanol, and n-propanol.

Syngas is passed via line 102 to slot injector 104 for introduction into deep tank bioreactor 106. The syngas may from time-to-time contain hydrogen cyanide. Bioreactor 106 contains fermentation broth containing microorganisms for the bioconversion of syngas to ethanol. The fermentation broth also contains nutrients for the microorganisms. Slot injector 104 introduces the syngas as microbubbles into the bottom of bioreactor 106, and the microbubbles pass upwardly through the fermentation broth during which time hydrogen, carbon monoxide, and carbon dioxide gas into the fermentation broth for uptake by the microorganisms and bioconversion to ethanol. At the top of bioreactor 106 an off-gas gas depleted in hydrogen and carbon monoxideexits via line 108.

A portion of the fermentation broth is continuously withdrawn from bioreactor 106 via line 110. A portion of the fermentation broth in line 110 is passed via line 112 to slot injector 104 as motive fluid, and another portion of the fermentation broth in line 110 is passed via line 116 to ethanol recovery operation 134. At least a portion of the aqueous stream subsequent to ethanol recovery is returned to bioreactor 106 via line 118. This return stream may contain dissolved components not separated during the recovery of ethanol including, but not limited to, dissolved metal cation and dissolved nutrients and adjuvants.

Continuously or intermittently a metal cation is provided to line 112 by line 114. Line 114, or separate lines, may also supply makeup water, nutrients and adjuvants such as components to maintain the sought pH of the fermentation broth, e.g., sodium hydroxide and buffers. The introduction of the metal cation may be limited to certain operations of the process such as during startup periods and during periods where the risk of hydrogen cyanide passing into the fermentation broth exists. As shown, the motive fluid being provided by line 112 is admixed with syngas being provided by line 102 to slot injector 104. Although the duration of the contact may be relatively short, at least a portion of the hydrogen cyanide contained in the syngas may be converted to insoluble metal complex prior to entry of the motive fluid into the fermentation broth.

As shown, the apparatus may be operated to maintain a predetermined concentration of dissolved metal cation in the fermentation broth, and may be operated to adjust the amount of metal cation being supplied to the fermentation broth based upon the concentration of hydrogen cyanide in the syngas. Probe 120 is adapted to determine the concentration of dissolved metal cation in the fermentation broth. Probe 120 may be, for instance, Inductively Coupled Plasma (ICP). Probe 120 is adapted to provide a signal, corresponding to the concentration of metal cation in the fermentation broth, to computer 124. The signal may be transmitted via line 122 or may be a wireless transmission. Computer 124 is adapted to determine the amount of metal cation needed to be passed to the fermentation broth in order to maintain the predetermined concentration of dissolved metal cation. This determination may be by any suitable technique, e.g., by a lookup table. Computer 124 is in communication with valve 130 which adjusts the flow rate of metal cation into line 114. This communication may be by line 132 are may be by wireless transmission. Typically, the metal cation is dissolved in an aqueous liquid to facilitate control of the flow of metal cation into line 114 and ultimately to the fermentation broth.

Probe 126 is adapted to determine the concentration of hydrogen cyanide in the syngas. Probe 126 may be, for instance, mass spectrometry, gas chromatography, Near-Infrared Cavity—Enhanced Laser Absorption Spectroscopy. Probe 126 is adapted to provide a signal corresponding to the concentration of hydrogen cyanide in the syngas. The signal may be transmitted via line 128 or may be a wireless transmission to computer 124. Computer 124 is adapted to calculate the amount of hydrogen cyanide being passed via line 102 to slot injector 104 based upon the concentration of hydrogen cyanide in the syngas as provided by probe 126 and a determination of the flow rate of syngas. The calculated amount of hydrogen cyanide being introduced is used by the computer to adjust the flow of metal cation in line 114 by controlling valve 130. This determination may be by any suitable technique, e.g., by a lookup table.

In further detail, ethanol recovery operation 134 comprises one or more unit operations to separate light gases such as hydrogen, nitrogen, carbon monoxide, and carbon dioxide from the fermentation broth, obtain a product stream comprising ethanol, and separate solids. As shown, the light gas separation yields a gas stream which is withdrawn from operation 134 by the gas effluent line 136 from operation 134. This light gas separation may be affected by any convenient unit operation, and often a flash separation is used. Ethanol is recovered by distillation in ethanol recovery operation 134 and exits via product stream 138. A solids stream can be recovered by centrifugation or as a concentrated still bottoms stream and is removed from ethanol recovery operation 134 via line 140. These solids include debris from the microorganisms and any insoluble metal complex of the metal cation and cyanide anion. The solids containing stream in line 140 may be treated in a digester operation prior to disposal. The aqueous stream recovered from ethanol recovery operation 134 is passed via line 118 to bioreactor 106. Ethanol recovery operation 134 may recover this aqueous stream in any suitable manner, including, but not limited to, phase separation from a solids containing stream.

By way of example and not in limitation of the invention, the apparatus described in the drawing is used to convert syngas to ethanol. The syngas contains about 5 ppm by volume hydrogen cyanide. The syngas is introduced into a deep tank bioreactor using a slot injector where the motive fluid is a recycle stream of fermentation broth. The deep tank bioreactor has a fermentation broth depth of about 18 meters.

Ferrous nitrate is used as the metal cation and is supplied to the fermentation broth with the motive fluid. The ferrous cation concentration in the motive fluid is approximately 6.2 ppm by weight per liter. The ferrous cation concentration in the fermentation broth is maintained at about 6.06 ppm by weight per liter. The recycle aqueous stream in line 118 contains about 6.23 ppm by weight per liter of ferrous cation.

During steady-state operation of the apparatus, about 45 percent of the amount of makeup metal cation needed to maintain the ferrous cation concentration in the fermentation broth is taken up by the cells, about 23 percent of this amount of metal cation is reacted with cyanide anion to form the insoluble metal complex, and the balance is lost due to other causes. The population of the microorganisms, which otherwise would have been substantially killed off by this large amount of hydrogen cyanide in the syngas, is substantially unaffected in comparison to a similar process in which the syngas contains less than about 0.01 ppm by volume hydrogen cyanide.

It is claimed:

1. A process anaerobic bioconversion of a gas substrate comprising carbon monoxide, hydrogen and carbon dioxide to an oxygenated organic compound in a fermentation broth wherein said gas substrate may contain from time to time hydrogen cyanide comprising:

a. continuously introducing said gas substrate into a fermentation broth containing microorganisms suitable for bioconverting said substrate to an oxygenated organic compound, said fermentation broth being maintained under anaerobic fermentation conditions, and the gas substrate having sufficient contact with the fermentation broth to provide an oxygenated organic compound-containing fermentation broth and a substrate-depleted gas phase;

b. maintaining the pH of the fermentation broth between about 4 and 6;

c. continuously or intermittently supplying to said fermentation broth a metal cation of one or more of iron, cobalt, nickel and zinc capable of forming a substantially water insoluble complex with a cyanide anion, to provide said metal cation dissolved in said fermentation broth in an amount at least stoichiometrically sufficient to form under said anaerobic fermentation conditions and pH said water insoluble complex with the cyanide anion if introduced with said gas substrate into said fermentation broth;

d. continuously withdrawing the substrate-depleted gas phase from the fermentation broth having a substantial absence of hydrogen cyanide; and e. continuously or intermittently withdrawing a portion of the fermentation broth for recovery of said oxygenated organic compound, said withdrawal being sufficient to maintain the oxygenated organic compound in said fermentation broth below a concentration that unduly adversely affects the microorganisms.

2. The process of claim 1 wherein the metal cation comprises at least one of iron and cobalt.

3. The process of claim 2 wherein the metal cation comprises ferrous cation.

4. The process of claim 1 wherein the pH of the fermentation broth is maintained at between about 4 and 5.5.

5. The process of claim 1 wherein the at least one metal cation is introduced into the fermentation broth at a rate sufficient to maintain a substantially constant concentration of dissolved metal cation in the fermentation broth.

6. The process of claim 1 wherein the concentration of hydrogen cyanide in the gas substrate being passed to the fermentation broth is determined and the rate of addition of the metal cation is adjusted in response to determined concentration of the hydrogen cyanide in the gas substrate to provide sufficient metal cation to complex cyanide anion.

7. The process of claim 1 wherein the oxygenated organic compound comprises alkanol.

8. The process of claim 7 wherein the alkanol comprises at least one of ethanol, propanol, and butanol.

9. A process anaerobic bioconversion of a gas substrate comprising carbon monoxide, hydrogen and carbon dioxide to an oxygenated organic compound in a fermentation broth wherein said gas substrate may contain from time to time hydrogen cyanide comprising:

a. continuously introducing said gas substrate into a fermentation broth by injection using a motive fluid, said fermentation broth containing microorganisms suitable for bioconverting said substrate to the oxygenated organic compound, said fermentation broth being maintained under anaerobic fermentation conditions, and the gas substrate having sufficient contact with the fermentation broth to provide an oxygenated organic compound-containing fermentation broth and a substrate-depleted gas phase;

b. maintaining the pH of the fermentation broth between about 4 and 6;

c. continuously or intermittently supplying to said motive fluid a metal cation of one or more of iron, cobalt, nickel and zinc capable of forming a substantially water insoluble complex with cyanide anion, to provide said metal cation dissolved in said fermentation broth in an amount at least stoichiometrically sufficient to form, under said anaerobic fermentation conditions and pH, said water insoluble complex with the cyanide anion if introduced with said gas substrate into said fermentation broth;

d. continuously withdrawing the substrate-depleted gas phase from the fermentation broth having a substantial absence of the hydrogen cyanide; and e. continuously or intermittently withdrawing a portion of the fermentation broth for recovery of said oxygenated organic compound, said withdrawal being sufficient to maintain the oxygenated organic compound in said fermentation broth below a concentration that unduly adversely affects the microorganisms.

10. The process of claim 9 wherein the motive fluid comprises a recycle stream of fermentation broth.

11. The process of claim 10 wherein the injection is via at least one slot injector.

12. The process of claim 10 wherein the at least one metal cation is introduced into the motive fluid at a rate sufficient to maintain a substantially constant concentration of dissolved metal cation in the fermentation broth.

13. The process of claim 10 wherein the concentration of hydrogen cyanide in the gas substrate being passed to the fermentation broth is determined and the rate of addition of the metal cation is adjusted in response to determined concentration of the hydrogen cyanide in the gas substrate to provide sufficient metal cation to complex cyanide anion.

14. The process of claim 10 wherein the concentration of dissolved metal cation in the fermentation broth is between about 0.25 and 0.5 milligram atoms per liter.

15. The process of claim 14 wherein the metal cation comprises ferrous cation.

16. The process of claim 13 wherein at least about 0.42 gram atoms of metal cation are provided per unit time per mole of hydrogen cyanide contained in the gas substrate introduced per unit time into the fermentation broth and the metal cation comprises ferrous cation.

17. The process of claim 15 wherein the metal cation is present in a concentration of between about 10 and 50 times that required for the stoichiometric reaction to form the water insoluble complex.

18. The process of claim 15 wherein the fermentation broth is contained in a deep tank bioreactor and the gas substrate is injected into the fermentation broth as microbubbles.

19. The process of claim 15 wherein the oxygenated organic compound comprises at least one of ethanol, propanol and butanol.

* * * * *